(12) United States Patent
Donaldson

(10) Patent No.: US 8,057,831 B2
(45) Date of Patent: Nov. 15, 2011

(54) DIGESTIVE/LAXATIVE COMPOSITIONS

(75) Inventor: Bruce William Donaldson, Auckland (NZ)

(73) Assignee: Vital Food Processors Limited, Auckland (NZ)

(*) Notice: Subject to any disclaimer, the term of this patent is extended or adjusted under 35 U.S.C. 154(b) by 840 days.

(21) Appl. No.: 10/247,721

(22) Filed: Sep. 20, 2002

(65) Prior Publication Data

US 2004/0058025 A1    Mar. 25, 2004

Related U.S. Application Data

(63) Continuation of application No. PCT/ZN01/00044, filed on Mar. 21, 2001.

(30) Foreign Application Priority Data

Mar. 21, 2000 (NZ) .......................... 503500

(51) Int. Cl.
*A61K 35/78* (2006.01)
(52) U.S. Cl. ...................................... 424/777
(58) Field of Classification Search .......... 424/1
See application file for complete search history.

(56) References Cited

U.S. PATENT DOCUMENTS

| | | | | |
|---|---|---|---|---|
| 2,854,376 A | * | 9/1958 | Hardt | 514/517 |
| 4,104,414 A | * | 8/1978 | Rahman et al. | 426/599 |
| 4,999,200 A | * | 3/1991 | Casillan | 424/480 |
| 5,298,275 A | * | 3/1994 | Balasingham et al. | 426/599 |

FOREIGN PATENT DOCUMENTS

| | | | |
|---|---|---|---|
| CN | 1107308 A | | 8/1995 |
| EP | 0 424 999 A1 | * | 5/1991 |
| EP | 0485193 A1 | * | 5/1992 |
| NZ | 191708 | | 11/1981 |
| NZ | 235 972 | | 5/1992 |

OTHER PUBLICATIONS

Donaldson, B., Kiwifruit Extract Provides Natural Relief (Press Release-Foundation for Research, Science and Technology), Scoop Media [online], Feb. 12, 2000, retrieved from the internet: <URL: http://www.scoop.co.nz/stories/sc0002/s00019.htm.*
Cyberchemist, Zylax—Natural Digestive Enhancer, Product Information, Retrieved from the internet on Feb. 25, 2005 from <URL: http://www.chemist.co.nz/product.cfm?productID=4610 &GroupID=1&CategoryID=157&SubcatID=24.*
Morton, J. 1987. Kiwifruit. p. 293-300. In: Fruits of warm climates. Obtained online on Mar. 30, 2007 at <http://www.hort.purdue.edu/newcrop/morton/kiwifruit_ars.html>.*
Overgaard et al, Patients Evaluation of Shape, Size, and Color of Solid Dosage Forms, Pharm Worl Sci 2001; 23(5): 185-188.*
Donaldson, B., Kiwifruit Extract Provides Natural Relief (Press Release), Scoop Media [online], Feb. 12, 2000, [retrieved on Jun. 12, 2001]. Retrieved from the internet: <URL: http://www.scoop.co.nz/stories/SC0002/S0019.htm.
Donaldson, B., Natural Relief, Technology NZ—Media Releases [online], Mar. 1, 2000, [retrieved on Jun. 15, 2001]. Retrieved from the Internet: <URL: http//www.technz.co.nz/technz/media/2000/media153.htm.
Technology New Zealand, kiwifruit Enzyme on the Job, Technology NZ-Publications [online], Apr. 11, 2000 [retrieved on Jun. 15, 2001]. Retrieved from the Internet:<URL: http://www.technz.co.nz/technz/texpress/te_apr00.htm.
Chen, J. D. et al., The efects of Actinidia Sinensis Planch (kiwi) drink supplementation on athletes training in hot environments, J of Sports Medicine and hpysical Fitness, 1990, vol. 30, No. 2, pp. 181-184.
Vital Foods Limited, Zylax, Vital Foods website [online], [retrieved on Jun. 12, 2001]. Retrieved from the Internet: <URL: http://www.vitalfoods.co.nz/page2.html.

* cited by examiner

*Primary Examiner* — Tracy Vivlemore
*Assistant Examiner* — Jennifer Berrios
(74) *Attorney, Agent, or Firm* — Lowe Hauptman Ham & Berner LLP

(57) ABSTRACT

The use of actinidin as a digestive/laxative aid. Method of obtaining actinidin from fruit.

30 Claims, No Drawings

DIGESTIVE/LAXATIVE COMPOSITIONS

This application is a continuation of international application PCT/NZ01/00044 filed on Mar. 21, 2001, which is based on, and claims priority from New Zealand Patent Application Number 503500, filed on Mar. 21, 2000. The entire contents of the PCT/NZ01/00044 are incorporated herein by reference.

TECHNICAL FIELD

The present invention is directed to methods and compositions for aiding digestion and/or for promoting the regular evacuation of bodily solid waste matter. Described are digestive/laxative compositions and methods of manufacture and use of same. It is envisaged that the present invention may be particularly suitable for addressing digestive dysfunctions that suggest a malfunction of the mammalian gastro-intestinal system These symptoms include, but are not limited to, indigestion, gastric reflux, bloat, gas, abdominal pain, diarrhea, heart-burn, constipation, and irritable bowel syndrome. However, it is to be understood and appreciated that the invention is not to be limited to such use. Moreover, the prior art and possible applications of the invention as discussed below are therefore given by way of example only.

In this specification, the terms "digestive/laxative compositions" and "digestive aids" are used interchangeably.

BACKGROUND ART

In the human gastro-intestinal system, proteolytic enzymes operate by chopping the long chain complex amino acids that make up proteins found in food, into shorter chain, more simple amino acids which can then pass into the cells lining the small intestine where they are further processed into fuel to provide the body with some of the necessary ingredients for growth and energy production.

Digestion is the whole complex biological process by which the body converts food to fuel. The more efficient the digestion process, the more energy the body derives from a given quantity of food.

Only raw food contains active enzymes. The process of cooking food deactivates most enzymes.

A fit healthy body produces most but not all the enzymes it requires for efficient digestion. The balance is derived from the food we eat. To prevent the body taking in too much additional enzyme by way of the food supply, there are mechanisms that operate to control the activity of the enzymes introduced in the food supply. These mechanisms operate as enzyme inhibitors.

For example, as saliva mixes with food during the chewing and swallowing process, excess enzymes in the food are targeted by enzyme suppressors in the saliva to ensure that the material entering the stomach will not cause an enzyme overload.

These mechanisms work well for a fit healthy body that produces its full quota of enzymes and is ingesting a diet high in raw fruit and vegetables.

However, many bodies are not as fit and healthy as nature designed them to be and therefore do not produce anywhere near enough enzymes for efficient digestion. In this case, the additional enzymes required from the diet are significantly greater than for a fit, active, younger person.

As we age, our commitment to fitness tends to diminish and the symptoms of enzyme depletion become more pronounced—indigestion, acid reflux, and constipation are all thought to be classic symptoms. There is even a school of thought that irritable bowel syndrome and divoticulitus could also be related to long term enzyme depletion.

Obviously the condition is exacerbated if we are incapacitated by sickness oar injury.

One would think that the most natural remedy would be to eat more raw fruit and vegetables. Whilst this may help, the enzyme suppressing mechanisms appear to accept only a limited increase, and suppress the activity of the balance.

This leads us to postulate that if a person is on a diet low in fresh fruit and vegetables and is showing symptoms of enzyme depletion then increasing the level of fresh fruit and vegetables in the diet may be sufficient to relieve the symptoms.

However if a person is on a diet comprising adequate levels of fresh fruit and vegetables, yet is still suffering symptoms of enzyme depletion (which is very common) it may well-be that the enzyme suppressing mechanisms will not permit enough additional enzyme from the diet to enter the system to correct the problem.

A number of digestive/laxative type compositions are known, many of which are based on synthetic materials or compounds. However, a significant number of persons requiring such compositions on a regular or semi-regular basis are also on other forms of medication. It is possible, in at least some of these instances, for there to be incompatibilities or conflicts between the medications—in the least serious scenario this may merely be a reduction in the effectiveness of one of the medications. In a more serious scenario, the health of the user could be compromised.

Further, some available digestive/laxative compositions may have unwanted side-effects, or may not be tolerated by the recipient. Accordingly there is a need for a greater choice of available digestive aids, as alternatives to those already available.

A current trend is also towards 'natural' type products. This trend among the health conscious consumer affects not only what they directly ingest, but also the cultivation or breeding of any foodstuffs they ingest. Organically grown produce and animal products are in demand in many markets. The administration of non-naturally occurring substances, especially if on a regular basis, is generally not allowable if the desired 'organic' labeling is to be applied to the end product.

It is an object of the present invention to address the foregoing problems or at least to provide the public with a useful choice.

Further aspects and advantages of the present invention will become apparent from the ensuing description which is given by way of example only.

BRIEF DESCRIPTION OF THE INVENTION

According to one aspect of the present invention there is provided a digestive/laxative composition including actinidin.

According to a further aspect of the present invention there is provided a digestive/laxative composition including actinidin contributed by the inclusion of fruit of genus *actinidia*, or a physiologically acceptable product thereof.

According to yet a further aspect of the present invention there is provided a digestive/laxative composition including fruit of the genus *actinidia*, processed according to a method in which the juice or pulp is processed at a temperature below that causing significant degradation of actinidin present.

According to an additional aspect of the present invention there is provided a digestive/laxative composition including fruit derived from the genus *actinidia*, processed according to a method in which the fruit is processed at a temperature below 40° C.

According to an additional aspect of the present invention there is provided a digestive/laxative composition including fruit derived from the genus *actinidia*, processed according to a method in which the fruit is processed at a temperature of about 40° C. to 40° C.

According to an additional aspect of the present invention there is provided a digestive/laxative composition including fruit derived from the genus *actinidia*, processed according to a method in which the fruit is processed at a temperature of about 10° C. and 10° C.

According to yet a further aspect of the present invention there is provided a digestive/laxative composition in which the proportion of actinidin present is from 1 to 30% by weight According to a further aspect of the present invention there is provided a method of preparing a digestive/laxative composition, including the steps of
(a) pulping fruit of the genus *actinidia*,
(b) clarifying the pulped material,
(c) subsequently lyophilising the pulped material.

According to a further aspect of the present invention there is provided a method of preparing a digestive/laxative composition, substantially as described above, wherein the pulping step is conducted using the "soft pulping" methodology as described in NZ Patent No. 235972.

According to a further aspect of the present invention there is provided a method of preparing a digestive/laxative composition, substantially as described above, wherein the clarifying step is conducted using centrifuge methodology.

According to an alternative aspect of the present invention there is provided a method of preparing a digestive/laxative composition, substantially as described above, wherein the clarifying step is conducted using freeze-concentrating methodology.

According to a further aspect of the present invention there is provided a method of preparing a digestive/laxative composition, substantially as described above, wherein the process is performed at a temperature and/or conditions which do not result in significant degradation of actinidin.

According to a further aspect of the present invention there is provided a method of preparing a digestive/laxative composition, substantially as described above, wherein the entire process is performed at a temperature of less than 40° C.

According to a further aspect of the present invention there is provided a method of preparing a digestive/laxative composition, substantially as described above, wherein the entire process is performed at a temperature of about 40° C. to 40° C.

According to a further aspect of the present invention there is provided a method of preparing a digestive/laxative composition, substantially as described above, wherein the entire process is performed at a temperature of about 10° C. to 10° C.

According to a further aspect of the present invention there is provided a method of preparing a digestive/laxative composition, substantially as described above, wherein the proportion of actinidin in the resulting product does not fall below 1% by weight.

According to a further aspect of the present invention there is provided a method of preparing a digestive/laxative composition, substantially as described above, wherein the proportion of actinidin in the resulting product is about 10% to 20% by weight.

According to a further aspect of the present invention there is provided a method of addressing digestive dysfunction including the step of administering a digestive/laxative composition including actinidin.

According to a further aspect of the present invention there is provided a method of addressing digestive dysfunction, substantially as described above, including the administration of a digestive/laxative composition, According to a further aspect of the present invention there is provided a method of addressing digestive dysfunction, substantially as described above, wherein the composition is manufactured by the methods substantially as described above.

According to a further aspect of the present invention there is provided a method of addressing digestive dysfunction, substantially as described above, wherein the administration of the composition is oral.

According to a further aspect of the present invention there is provided a method of addressing digestive dysfunction, substantially as described above, wherein the administration of the composition is conducted prior to a meal.

According to a further aspect of the present invention there is provided a method of addressing digestive dysfunction, substantially as described above, wherein the administration of the composition is undertaken approximately 30 minutes before a meal.

Trials and investigations by the applicant have determined that while raw, fresh kiwifruit can act as an effective digestive aid, these properties have not been observed to any great extent in processed kiwifruit (*Actinidia chinensis*) products. Furthermore, a prohibitive amount of raw kiwifruit must usually be ingested in order for the digestive effect or benefits to occur.

The prior art suggests that any digestive enhancing properties in the fruit are attributable to the fact that kiwifruit contains significant quantities of dietary fibre. This is an extrapolation of observed digestive/laxative properties in other fruit and has, until now, been regarded as the most significant factor giving rise to the digestive/laxative properties of the fruit. The applicant's research has shown this not to be the case.

The work of the applicant indicates that while the dietary fibre content of the fruit may contribute to any observable digestive/laxative properties, these properties should not disappear or severely diminish in processed kiwifruit products which nonetheless retain a significant dietary fibre content. Accordingly it was determined that there must be at least one other contributing factor to the digestive/laxative properties.

The applicant has been involved in pulp and juice extraction techniques for kiwi fruit processing. This is the subject of NZ Patent No. 235972. Pulp extract from this and similar processes was utilized in trial work. In a number of trials, extracted pulp and juice from kiwifruit was observed to retain the digestive characteristics of the fresh fruit. In further trials, seed was removed from the pulp and again the resulting product was observed to retain its digestive properties.

Further work indicated that the digestive effectiveness of the kiwifruit pulp was directly influenced by the "freshness" of the product. When the pulp was exposed to ambient temperature (20-30° C.) the color, flavor and odor of the pulp deteriorated slightly over time. It was observed that the digestive properties of the pulp appeared to diminish in relationship to the sensory deterioration (in appearance) of the pulp.

Fresh kiwifruit pulp was therefore refrigerated at 4° C. and it was noted that the rate of deterioration was significantly slower than at ambient temperatures. Trials were carried out that indicated the pulp retained some, if not all, of its digestive properties even after six days refrigeration at 4° C. From this it was concluded that the digestive properties of the pulp are apparently diminished by oxidation and that refrigeration slowed the rate of oxidation.

As the fruit is seasonal, it was decided that to commercially exploit the digestive properties of the pulp some form of long term storage would be required. Storage trials were undertaken involving three of the more conventional storage methods being (a) pasteurization, (b) preservation, (c) freezing.

The results of these trials indicated the following:
(a) Pasteurizing—exposing the pulp to 80° C. for 30 seconds—destroyed the digestive properties of the product,
(b) preservative—in the form of added potassium sorbate—combined with 4° C. refrigeration extended the shelf life of the pulp to approximately 20 days and the pulp retained some, if not all, the digestive properties; color of the pulp still deteriorated and it was suspected that the effective activity of the digestive "ingredient" may have deteriorated in tine with this but this has not been fully documented.
(c) freezing—the sooner this was undertaken after the manufacture of the pulp the "fresher" the resultant thawed product appeared. Also the faster the freezing process, the better the resultant product appeared with cryogenic/nitrogen freezing giving the best result. Little if any of the digestive characteristics of the fresh pulp were lost in the freezing process even with samples held frozen for two years.

Based on the analysis of the chemical composition of the kiwifruit pulp and these observations, the applicant deduced that the ingredient in the pulp most susceptible to heat degradation was the proteolytic enzyme actinidin which makes up approximately 1% of the composition of the fresh pulp. The applicant then extrapolated that it was in fact the enzyme actinidin that imparted the characteristic digestive properties to the kiwifruit pulp.

Actinidin was initially isolated from clarified kiwifruit juice using the method indicated in the paper Production of Actinium—a proteotytic enzyme from kiwifruit by M J Boland and D J W Burns (1980) and in the NZ Patent document No. 191708, Essentially the enzyme was isolated as follows:

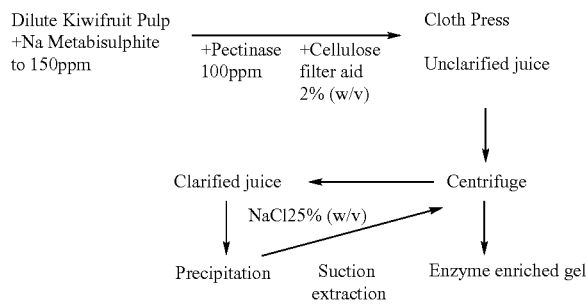

The enzyme enriched gel was tested for activity by placing a drop on a piece of undeveloped X-ray film. The liquid removed the purple colored coating of the film exposing the underlying celluloid.

Measured amounts of the gel were then spread on pieces of bread and the bread then eaten. The bread clearly possessed similar digestive characteristics as the fresh kiwifruit pulp. It was concluded therefore that the enzyme actinide was in fact the active ingredient, rather than dietary fibre as first thought.

From further trials it was possible to estimate that the yield of actinidin from between 50 g and 150 g of fresh kiwifruit pulp was sufficient to trigger a positive digestive effect and/or regulatory motion in the average adult.

Because the method described in the above referenced document and New Zealand Patent No. 191708 used reducing agents to minimize oxidation (which is not acceptable under some food regulations) we wished to develop a processing method that did not rely on the addition of a reducing agent.

We therefore utilized the "soft pulping" method as described in our New Zealand Patent No. 235972 in order to got the pulped fruit to the "unclarifed juice" stage as referred to in the preceding diagram.

From there, a first method was to centrifuge the product, followed by freeze drying. Both centrifuge processes and freeze drying processes are well known and need not be described in any further detail herein A second method was to take the unclarified juice, and put it through a freeze concentrating step, followed by the freeze drying step. Again, both freeze concentrating methodology and freeze drying methodology are well known and need not be described in any further detail herein.

The result was a dried product in the form of honeycomb-like slab. This was then milled into a powder and utilized as appropriate, for example being encapsulated, tableted or added to other products, and the like.

Throughout the whole process, and to obviate the need for reducing agents and the like, it was important to ensure the temperature was below that which causes significant degradation of actinidin present. Through research and trial we concluded that a temperature range of between −40° C. to 40° C. was such a temperature range. Furthermore, we found through further research and trials that a temperature range of slightly less than 0° C. produced a higher spec product than temperature ranges up to +10° C. Hence, a preferred temperature range, throughout the entire process, would be between approximately −10° C. to 10° C.

Preferably, the temperature range indicated above would be present during the entire process, including the storage of whole fruit prior to it being broken open and/or "soft pulped". In any case, it is essential to ensure that, once the fruit has been broken open, the temperature ranges indicated above (i.e. the range of −40° C. to 40° C.) are utilized throughout the entire process.

Digestive dysfunction is a common affliction for a significant portion of the population. Causes giving rise to the affliction are varied but include: a lack of exercise, inappropriate diet, and the necessity to use some forms of medication. The present invention provides a means for addressing these problems.

Moreover, because the present invention may (preferably) be administered in a fashion which bypasses the enzyme suppressing mechanism in the saliva (e.g. orally), it allows the concentrated enzyme to be released into the user's body more effectively than if the user had eaten, for example, fresh fruit and vegetables, and particularly kiwifruit. Furthermore, the present invention is much easier to ingest than having to eat significant amounts of raw kiwifruit.

BEST MODES FOR CARRYING OUT THE INVENTION

Kiwifruit (the fruit of the *actinidia chinensis* vine as well as others) contains many bioactive components including seratonin and several enzymes. Predominant amongst these is the proteolytic enzyme actinidin. The molecular weight of actinidin is 28 kDa.

Actinidin belongs to a family of cysteine proteinases that include Papain from Papaya and Bromilain from Pineapple stem.

Whilst these enzymes belong to the same family, as with all enzymes, each has a unique range of operating criteria. This applies especially to the peptide bonds they cleave and the temperatures and acidity conditions they can tolerate.

In the mammalian gastrointestinal system, naturally occurring proteolytic enzymes assist the digestion process by chopping the long chain complex amino acids, that make up proteins found in food, into shorter chain, more simple amino acids capable of being absorbed by the cells lining the small intestine where they are further processed into fuel to provide the body with some of the necessary ingredient for growth and energy production.

Disruption of the normal bodily function caused by trauma, medication, confinement or other causes will often disrupt the normal process of digestion giving rise to digestive dysfunction. Symptoms of this dysfunction include (amongst others), indigestion, acid reflux, heartburn, bloat, gas, abdominal pain, diarrhea and constipation.

The invention includes the use of the proteolytic enzyme actinidin which can be extracted from kiwifruit and stabilized in a commercially useable form—this can then be used as a digestive aid, stimulant, regulator or laxative. As a natural product derived from a commonly consumed fruit it has no observed side effects and possesses no known health threat to consumers except possibly to a small proportion who may have an allergy to *actinidia*, fruit. Moreover, our trials with known kiwifruit allergy suffers have shown no allergic reaction to our product.

The methods used to manufacture the digestive/laxative composition utilizes some of the "soft pulping" technology referred to in NZ Patent 235972 to produce a pulpy green kiwifruit juice, which was then clarified and lyophilised, as described previously The method that utilized a centrifugal stage followed by the freeze drying stage generally gave a dry yield of less than 2% with an activity coefficient of 15,000 units. This type of yield appeared fairly consistent at all temperatures below 10° C. (but above −40° C.)—but achieved best yields in. the range 0° C. to 10° C.

The second method described previously in which the fruit was put through a freeze concentrating stage followed by the freeze drying stage, resulted in yields of 3% with an activity coefficient in excess of 22,000 units. It was found that this second method produced higher yields at temperatures less than 0° C. (but above −40° C.)—but achieved best yields in the range of −10° C. to 0° C. The product that resulted from the method as described above was essentially a dried product in the form of a honeycomb-like slab. This was then milled into a powder and combined with known tableting aids or additives and encapsulated or tableted.

This process enabled the researchers to manufacture the digestive/laxative composition without the addition of any reducing agent thus ensuring the resulting product could meet "organic certification" specifications as defined by the international agency IFOAM Some of the specific factors employed in the production method to prevent the degradation of the enzyme activity of actinidin are as follows:

Processing and storage temperatures preferably not being above 40° C. arid preferably kept well below this critical level (preferably in the range of −40° C. to 40° C., and more preferably in the range of −10° C. to 10° C.), Every effort is made throughout the process to minimize the extent of oxidation as the enzyme activity of actinidin has been recorded by the researchers to drop by 70% within 15 minutes of pulping, from a level of around 30,000 units/kg in fresh fruit to approximately 9,000 units in fruit that has been pulped at 21° C.

The addition of an appropriate reducing agent will minimize the extent of oxidation and other researchers have used this method successfully but as many reducing agents are not acceptable substance under some food regulations, we have developed a processing method that does not rely on the addition of a reducing agent.

So whilst the first laboratory trial undertaken to test the theory that actinidin can be beneficial in the treatment of digestive dysfunctions using a relatively pure form of actinidin extracted using the method outlined in NZ Patent 191708, the applicant has been careful to design a commercial processing method that is unlikely to damage the activity of this and other enzymes known to be present in the extract as these have the potential to extend the efficacy of the digestive/laxative composition.

The activity coefficient of the digestive/laxative composition has been calculated by reacting 20 mL of re-hydrated product with 3 ml of 50 $\mu$M phosphate buffer containing 0.1 $\mu$M N-$\alpha$-carbobenzyloxy-1-Lysine p nitrophenyl ester in an optical cell. The rate of production of p-nitro phenol was captured by absorption spectrophotometery using a Shimadzu UV-1201 spectrophotometer at 348 nm.

The preferred amount of active enzyme necessary to promote the digestive/laxative effect differs for different people, but appears to be approximately from 10 mg to 250 mg during a day. However, there appears to be a wide tolerance level and little by way of any adverse response to levels 2-10 times those indicated above.

A small group of trialists, with symptoms of digestive dysfunction, were provided with gelatin capsules containing 350 mg of the digestive/laxative composition (which includes approximately 60 mg of actinidin—a preferred ratio of actinidin within a capsule) with a minimum enzyme activity of 15,000 units/kg fw (1 unit hydolyses 1 millimole of N-$\alpha$-carbobenzoxy-l-lysine p-nitrophenyl ester per minute at 25° C., and 6 pH).

In the embodiment described above the amount, by weight, of actinidin in a 350 milligrams gelatin capsule is 60 milligrams, that is, approximately 17% by weight. The remaining approximately 83% by weight of the gelatin capsule may comprise or include some processed pulp from the original kiwifruit pulp, together with the addition of any known tableting aids, flavoring agents, texture improving agents, product improving additives, and the like. Such tableting aids and additives are well known and utilized for many vitamin and mineral preparations (for example Vitamin C capsules or tablets), and need not be described in any further detail here. Any amounts or ratios of these optionally additives may be utilized as required or as desired or as it is determined by the intended use of the composition or by health regulations.

Preferably, the digestive/laxative composition may be administered orally, and preferably before eating a meal. It is envisaged that a time period of approximately 15-45 minutes prior to eating would be the most effective time to take the digestive/laxative composition prior to the meal.

In one trial trialists were advised to take 2 of the above described capsules prior to each meal and drop back to 2 per day once they had achieved a noticeable improvement in terms of digestive dysfunction or regulatory.

Whilst the trial was originally established to test the efficacy of the product to reduce the incidence of constipation, several of the trialists reported that over the course of the trial (3 months) they experienced relief from a wide range of symptoms of digestive dysfunction including acid reflux, chronic constipation and clinically diagnosed IBS. This was a surprising and pleasing result.

A significant number of the trialists reported sustained improvement in their condition and six months after the conclusion of the trial, continued to use the product regularly.

It is known that actinidin tolerates a wide pH range (3-8) making it particularly suitable for use as a dietary supplement to enhance mammalian digestion. It can survive passage through the highly acidic (pH 3+) conditions of the stomach and operate most effectively in the higher pH conditions of the small intestine—the main site of protein digestion under normal circumstances.

In summary, some specific examples of embodiments of the invention include (but are riot restricted to):

- digestive/laxative composition including actinidin. This may include added actinidin from a synthetic and/or natural source.
- a digestive/laxative composition including actinidin contributed by the inclusion of fruit of genus *Actinidia*, or a product thereof. It is envisaged that the most commonly used fruit will be that of commercially grown kiwifruit (*Actinidia chinensis*).
- a digestive/laxative composition including juice or pulp derived from fruit of the genus *actinidia*, processed according to a method in which the juice or pulp is processed at a temperature below that causing significant degradation of actinidin present. Typically this will be below 40° C. Temperatures of −40° C. to 40° C. will be preferred.
- a digestive/laxative composition in which the proportion of actinidin present is from 5 to 30% by weight. More preferably this may be approximately 15°10.
- a method of addressing a digestive dysfunction including the administration of a composition including actinidin, preferably oral administration.
- a method of addressing a digestive dysfunction in which the administration of actinidin is from 10-250 mg actinidin per day—This may vary according to whether the invention is being used in a curative, or preventative, sense.
- a method of preparing a digestive composition including the removal of skin from the fruit of genus *actinidia*, preferably pulping the flesh of the fruit, subjecting the pulped material to a centrifugal step or a freeze concentrating step, optionally including any additional carriers. flavoring agents, texture improving agents, or product improving additives; optionally including additional actinidin, and wherein the entire process is performed at a temperature and/or conditions which do coot result in significant degradation of included actinidin.
- a method of manufacture in which the flesh of the fruit is maintained at a temperature of below 40° C. throughout the process. More preferably the temperature is between −40° C. to 40° C.
- a method of manufacture in which the conditions are such that the proportion of actinidin in the resulting product does not fall below 1% by weight.
- a method of addressing a digestive dysfunction comprising the administration of actinidin. preferably this is in the form of a composition as described above, and preferable derived from fruit of the genus *actinidia*.

Actinidin can be isolated and presented as a digestive aid in a variety of ways including but not limited to the following:
- incorporated in frozen or chilled desserts;
- blended with sugar or prepared as a sprinkle on product for use on breakfast cereals and
- incorporated into a wide variety of drinks and beverages;
- blended with mills or cream;
- blended with yoghurt, or ice cream;
- encapsulated and administered orally or as a suppository;
- pressed into tablet form to be administered orally.

The use of the product includes both human and animal use. Apart from the foregoing examples, administration may also be by way of a capsule, a drench or a suppository.

Aspects of the present invention have been described by way of example only and it should be appreciated that modifications and additions may be made thereto without departing from the scope thereof as defined in the appended claims The claims defining the invention are:

1. A method of treating digestive dysfunction comprising orally administering to a patient in need thereof an oral composition in the form of a tablet or capsule comprising about 1 to 30% by weight of actinidin together with pulp, at least a portion of said pulp being pulp of a fruit of genus *Actinidia*, and wherein said composition is obtained by processing said fruit at a temperature in the range of −10° C. to 10° C. to prevent significant degradation of actinidin.

2. A method as claimed in claim 1 wherein when the actinidin is present in said composition in a proportion of about 1 to 30% by weight, a balance of said composition comprises said pulp.

3. A method as claimed in claim 1 wherein the actinidin is present in said composition in a proportion of about 10 to 20% by weight.

4. A method as claimed in claim 1 further comprising administering said composition before a meal.

5. A method as claimed in claim 1 further comprising administering about 10 to 250 mg of said actinidin per day.

6. An oral composition in the form of a tablet or capsule suitable for treating digestive dysfunction comprising about 1 to 30% by weight of actinidin together with processed pulp that has been recovered from fruit of the genus *Actinidia*.

7. A composition as claimed in claim 6, wherein said composition has been produced by:
   (a) pulping fruit of the genus *Actinidia* to produce a pulped material,
   (b) clarifying the pulped material to produce a clarified pulped material, and
   (c) freeze drying the clarified pulped material,
   wherein the steps (a) to (c) of said method are performed at a temperature of about minus 10° C. to plus 10° C., such that substantial degradation of actinidin is prevented.

8. A method as claimed in claim 1 wherein the pulp in the tablet or capsule is freeze dried pulp.

9. A method as claimed in claim 8 wherein the freeze dried pulp comprises about 83% w/w of the tablet or capsule.

10. A method as claimed in claim 9 wherein the actinidin is present in said composition in a proportion of about 17% by weight.

11. A method as claimed in claim 10 wherein the tablet or capsule weighs about 350 mg.

12. A method as claimed in claim 11 wherein the tablet or capsule contains about 60 mg of actinidin.

13. A method as claimed in claim 1 wherein the oral composition is administered orally from about 15 to 45 minutes prior to eating a meal.

14. A method as claimed in claim 10 wherein the oral composition is administered orally about 30 minutes prior to eating a meal.

15. A method of preparing a digestive/laxative composition comprising from about 1% to 30% by weight of actinidin, comprising the steps of:

(a) selecting fruit of the genus *Actinidia* containing an effective amount of the enzyme actinidin,
(b) pulping the fruit to produce a pulped material,
(c) clarifying the pulped material to produce a clarified pulped material,
(d) freeze drying the clarified pulped material to produce a freeze dried pulped material,
(e) milling the freeze dried pulped material into a powder containing both the active enzyme actinidin and the milled freeze dried pulped material, and
(f) forming the powder into a tablet or capsule suitable for oral administration to a human,
wherein at least steps (b) to (c) of said method are performed at a temperature of about minus 10° C. to about 0° C., such that substantial degradation of actinidin is prevented.

16. A method as claimed in claim 15, wherein said steps (a) to (e) are carried out without the addition of a reducing agent.

17. A method as claimed in claim 16, wherein said pulped material is clarified by centrifugation.

18. A method as claimed in claim 16, wherein said pulped material is clarified by freeze-concentrating.

19. A method as claimed in claim 18 wherein the proportion of actinidin in the resulting composition is at least about 3% by weight.

20. A method as claimed in claim 19 wherein the proportion of actinidin in the resulting composition is about 10% to 20% by weight.

21. A method as claimed in claim 20 wherein the proportion of pulped material in the tablet or capsule is about 83% w/w.

22. A method as claimed in claim 21 wherein the powder is mixed with a product chosen from the group comprising tabletting aids, flavouring agents, texture improving agents, and product improving additives, before being formed into said tablet or capsule.

23. An oral composition as claimed in claim 6 wherein the proportion of actinidin in the resulting composition is about 10% to 20% by weight.

24. An oral composition as claimed in claim 6, wherein the tablet or capsule contains milled freeze dried processed pulp recovered from the genus *Actinidia*.

25. An oral composition as claimed in claim 6, wherein the proportion of processed pulp in the tablet or capsule is at least 70% by weight.

26. An oral composition as claimed in claim 25, wherein the capsule is a gelatin capsule.

27. An oral composition as claimed in claim 26, wherein the proportion of processed pulp in the capsule is about 83% by weight.

28. An oral composition as claimed in claim 27, wherein the proportion of actinidin in the capsule is about 17% by weight.

29. An oral composition as claimed in claim 25, wherein the oral composition also contains a product chosen form the group comprising tabletting aids, flavouring agents, texture improving agents, and product improving additives.

30. A method as claimed in claim 1 wherein, when the actinidin is present in said composition in a proportion of about 1 to 30% by weight, a balance of said composition comprises about 99 to 70% by weight of said pulp.

* * * * *